United States Patent
Mashak et al.

(10) Patent No.: US 7,591,267 B2
(45) Date of Patent: Sep. 22, 2009

(54) ROOM TEMPERATURE HEAT EXCHANGER FOR BREATHING CIRCUIT

(75) Inventors: James N. Mashak, Sun Prairie, WI (US); Scott A. Inman, Madison, WI (US); Denise L. Pernetti, Cottage Grove, WI (US); Robert Q. Tham, Middleton, WI (US)

(73) Assignee: General Electric Company, Schenectady, NY (US)

( * ) Notice: Subject to any disclaimer, the term of this patent is extended or adjusted under 35 U.S.C. 154(b) by 370 days.

(21) Appl. No.: 11/220,333

(22) Filed: Sep. 6, 2005

(65) Prior Publication Data

US 2007/0051367 A1 Mar. 8, 2007

(51) Int. Cl.
*A62B 7/10* (2006.01)
*A62B 23/02* (2006.01)

(52) U.S. Cl. ............. 128/205.28; 128/911; 128/203.12; 128/203.13; 128/201.13; 165/80.3; 165/104.21; 165/104.33

(58) Field of Classification Search ............ 128/205.28, 128/911, 203.12, 203.13, 201.13; 165/80.3, 165/104.21, 104.33
See application file for complete search history.

(56) References Cited

U.S. PATENT DOCUMENTS 2,990,695 A * 7/1961 Leffingwell, Jr. ............. 62/223
6,523,538 B1 * 2/2003 Wikefeldt ............. 128/204.18

FOREIGN PATENT DOCUMENTS

| GB | 2118047 A | 2/1983 |
|---|---|---|
| WO | 01/49351 A2 | 7/2001 |
| WO | 01/49351 A3 | 7/2001 |

OTHER PUBLICATIONS

Search Report, Application No. GB0617322.3, Dec. 22, 2006.

* cited by examiner

*Primary Examiner*—Patricia M Bianco
*Assistant Examiner*—Nihir Patel
(74) *Attorney, Agent, or Firm*—Andrus, Sceales, Starke & Sawall, LLP

(57) ABSTRACT

A breathing circuit for use with a ventilated patient that includes a heat exchanger for removing water vapor from the breathing gases to prevent condensation within the breathing circuit. The heat exchanger is positioned downstream from the $CO_2$ absorber and receives the breathing gases from the $CO_2$ absorber prior to delivery of the breathing gases to the inspiration limb of the patient circuit. The heat exchanger includes a plurality of inflow tubes and outflow tubes that are each open to a sump removably attached to the heat exchanger. The sump collects the water vapor condensed from the breathing gases within the heat exchanger.

17 Claims, 3 Drawing Sheets

US 7,591,267 B2

ROOM TEMPERATURE HEAT EXCHANGER FOR BREATHING CIRCUIT

BACKGROUND OF THE INVENTION

The present invention generally relates to a breathing circuit having a device for removing entrained water vapor from the breathing gas within the breathing circuit. More specifically, the present invention relates to a heat exchanger positioned within the breathing circuit to reduce the condensation at other areas within the breathing circuit.

A mechanical ventilator is often used to supply and remove breathing gases from a patient. The operation of the ventilator may be to assist and/or replace the natural breathing action of the patient, either alone or with the supply of an anesthetic agent to the patient. A typical mechanical ventilator has an inspiration limb for supplying breathing gases to the patient and an expiration limb for receiving breathing gases from the patient. The inspiration and expiration limbs are connected to arms of a Y-connector. A patient limb extends from a third arm of the Y-connector to an intubation tube or facemask for the subject.

A common type of mechanical ventilator recirculates the expired breathing gases from the patient through a $CO_2$ absorber back to the inspiration limb for rebreathing by the subject. A closed breathing circuit prevents the loss of anesthetic agents to ambient air. However, the $CO_2$ absorber in such a circuit creates an exothermic reaction that heats the breathing gas and entrains additional water vapor into the breathing gas. As an example, an additional 15 mg of water per breath become entrained in the breathing gases circulating through the $CO_2$ absorber in the closed breathing circuit.

Although it is preferable that the patient breathe moist, warm breathing gases, the presence of vapor in the breathing circuit creates several disadvantages. Specifically, when the warm, moist breathing gases expired by the patient, which are at body temperature, pass through the breathing circuit, which is at room temperature, the water vapor in the breathing gases condenses on components of the breathing circuit. As the breathing of the patient continues, the condensed water accumulates, which may interfere with the operation of valves, sensors or other components of the breathing circuit. Additionally, the breathing gases exiting the $CO_2$ absorber are at an elevated temperature relative to room temperature. As the breathing gases move further through the breathing circuit, the breathing gases cool and the water vapor entrained within the breathing gases can condense and accumulate within the breathing circuit.

Various solutions have been proposed to remedy this problem. Water traps may be inserted into the breathing circuit near problematic areas in an effort to accumulate water and prevent the water from reaching critical components. These water traps simply react to the problem and must be constantly monitored and emptied when the water traps become full.

Another solution is to heat the breathing circuit to prevent condensation of the water vapor. Heating of the breathing circuit may be carried out by resistance heaters, such as wires that are wrapped around the tubing of the limbs and around the sensors and valves. The heating device adds to the complexity of the breathing circuit and is often times not desired.

One specific example of a system designed to remove water vapor from breathing gases within the breathing circuit is shown and described in U.S. Pat. No. 6,619,289, the disclosure of which is incorporated herein by reference. In the '289 patent, a carbon dioxide absorber canister includes an integral moisture sump that collects condensate from areas of the breathing circuit that are difficult to drain, such as the carbon dioxide absorber canister itself.

Although the integral moisture sump within the carbon dioxide absorber canister is an effective way to remove some of the water vapor, an approach that removes additional volumes of water vapor from the breathing gas is highly desirable. Specifically, an approach that reduces the temperature of the breathing gas after the $CO_2$ absorber without the use of any additional operating components is particularly desirable.

SUMMARY OF THE INVENTION

The present invention is related to a breathing circuit for a patient that includes a heat exchanger for removing water vapor and heat from breathing gases within the breathing circuit.

The breathing circuit includes an inspiration limb that provides breathing gases to a patient. Breathing gases from the patient are received with an expiration limb that directs the breathing gases from the patient to a $CO_2$ absorber. The $CO_2$ absorber is positioned within the breathing circuit to receive the breathing gases from the expiration limb and remove $CO_2$ from the breathing gases prior to rebreathing by the patient. The $CO_2$ absorber removes $CO_2$ through an exothermic reaction that supplies both heat and water vapor to the breathing gases within the breathing circuit.

The breathing circuit includes a heat exchanger positioned downstream from the $CO_2$ absorber to receive the breathing gases from the $CO_2$ absorber. The heat exchanger is operable to reduce the temperature of the breathing gases and remove moisture from the breathing gases prior to delivery of the breathing gases to the inspiration limb. The heat exchanger includes a plurality of inflow tubes that each receive the breathing gases from the $CO_2$ absorber. The inflow tubes direct the breathing gases to a set of outflow tubes that deliver the breathing gases to the inspiration limb. As the breathing gases pass through the inflow and outflow tubes, the tubes are in contact with ambient, room temperature air which is at a lower temperature than the breathing gases. The heat exchanger tubes allow heat to be transferred from the breathing gases to ambient air, thus reducing the temperature of the breathing gases and causing water vapor to condense along the inner surfaces of the inflow and outflow tubes.

Each of the inflow and outflow tubes is in communication with a sump positioned at a bottom end of the heat exchanger. The sump is positioned to collect water condensed out of the breathing gases while the breathing gases pass through the heat exchanger. The sump is removably attached to the heat exchanger and includes a drain that allows the collected water to be removed from the sump.

The heat exchanger positioned within the breathing circuit removes water vapor and reduces the temperature of the breathing gases prior to the breathing gases contacting various sensors and components within the breathing circuit downstream from the heat exchanger. The heat exchanger thus prevents undesired condensation within various areas of the breathing circuit.

BRIEF DESCRIPTION OF THE DRAWINGS

The drawings illustrate the best mode presently contemplated of carrying out the invention. In the drawings.

DETAILED DESCRIPTION OF THE PREFERRED EMBODIMENT

Figure 1:
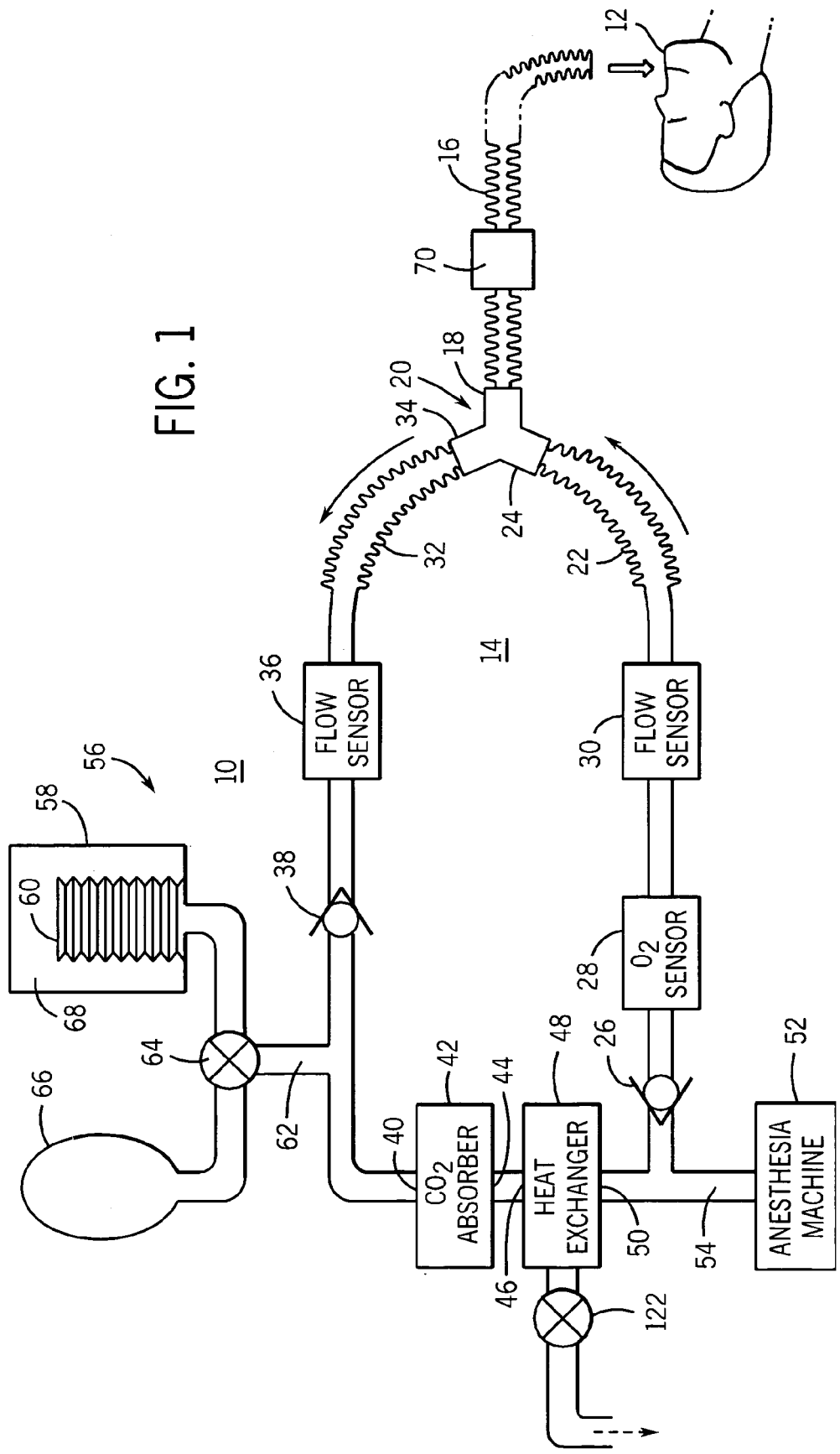
FIG. 1 is an overview of a ventilator breathing circuit showing the preferred placement of the heat exchanger.

FIG. 1 illustrates a ventilation system 10 for mechanically ventilating a patient 12. The ventilation system 10 includes a closed breathing circuit 14. The closed breathing circuit 14 includes a patient limb 16 that delivers breathing gases to the patient 12 from a first leg 18 of a Y-connector 20.

The breathing circuit 14 includes an inspiration limb 22 connected to the inlet leg 24 of the Y-connector 20. The inspiration limb 22 receives the flow of breathing gases to be supplied to the patient 12 through a check valve 26. In the embodiment of the invention illustrated, an oxygen sensor 28 and a flow sensor 30 are positioned between the check valve 26 and the inspiration limb 22.

The closed breathing circuit 14 includes an expiration limb 32 connected to the outlet leg 34 of the Y-connector 20 to receive the exhaled breathing gases from the patient. The exhaled breathing gases pass through a flow sensor 36 and a check valve 38. The expiration limb 32 is connected to the inlet 40 of a carbon dioxide ($CO_2$) absorber 42. In a conventional closed breathing circuit, the outlet 44 of the $CO_2$ absorber 42 is connected to the inspiration limb 22 to complete the closed breathing circuit. In the embodiment of the invention illustrated in FIG. 1, the outlet 44 of the $CO_2$ absorber 42 is connected to the inlet 46 of a heat exchanger 48, the details of which will be described in greater detail below.

The $CO_2$ absorber 42 is a conventional component that may contain soda lime or other suitable $CO_2$ absorbent. As the expired breathing gases from the patient pass through the $CO_2$ absorber 42, an exothermic reaction takes place which both heats the breathing gases and entrains additional moisture within the breathing gas.

As illustrated in FIG. 1, the breathing gases from the outlet 50 of the heat exchanger 48 flow through the check valve 26 and eventually into the inspiration limb 22. An anesthesia machine 52 may be connected to the inspiration limb 22 by a conduit 54 to supply and maintain an anesthetic agent into breathing gases within the circuit 14.

The breathing circuit 14 shown in FIG. 1 includes means 56 for circulating the breathing gases throughout the system. In the embodiment of the invention illustrated, the means 56 is a ventilator including a bellows assembly 58. The bellows assembly 58 includes an expandable, pleated bellows 60 connected to the expiration limb 32 by a conduit 62. The conduit 62 includes a switching valve 64 that allows the driving force for the breathing gases to be selected between the bellows 60 and a handbag 66.

During expiration of the patient, the driving gas in the housing 68 of the bellows assembly 58 is allowed to exit, allowing the bellows 60 to expand upwardly and receive the exhaled gases as the patient 12 breathes out. The exhaled gases are provided to the bellows 60 by the expiration limb 32 and the switching valve 64.

On the next breath of the patient 12, the bellows 60 is compressed by the driving gases within the housing 68 to provide breathing gases to the patient through the $CO_2$ absorber 42, heat exchanger 48 and the inspiration limb 22. The $CO_2$ in the breathing gases previously exhaled by the subject are removed by the $CO_2$ absorber 42.

The breathing circuit may include various sensors, such as the flow sensors 30, 36, qualitative gas sensors, such as the oxygen sensor 28, and various pressure sensors that monitor the operation of the breathing circuit 14. The patient limb 16 will typically include breathing gas sampling tubes for the sensors, a bacterial filter and other elements, collectively shown by reference numeral 70.

As show in FIG. 1, the breathing circuit 14 includes the heat exchanger 48 inserted in the breathing circuit 14 downstream from the $CO_2$ absorber 42 and upstream from the inspiration limb 22. As described previously, the heat exchanger 48 includes an inlet 46 that receives the warm, moist, exhaled breathing gases that have been scrubbed of $CO_2$ by the $CO_2$ absorber 42. In a typical embodiment, the breathing gases leaving the outlet 44 of the $CO_2$ absorber has a temperature in the range of 37° C. Since typical room temperature is approximately 21° C., the temperature differential between the breathing gases within the breathing circuit 14 and the room is approximately 16° C. when measured at the outlet 44 of the $CO_2$ absorber 42.

In a closed breathing circuit not including the heat exchanger 48, the warm, moist breathing gases from the $CO_2$ absorber 42 pass over the relatively cold, room temperature surfaces of the various sensors and tubing contained within both the inspiration limb 22 and the patient limb 16, which cools the breathing gases and causes moisture to condense out of the breathing gases and collect on the sensing equipment. The heat exchanger 48 is positioned between the $CO_2$ absorber 42 and the inspiration limb 22 to reduce the temperature of the breathing gases and remove moisture from the water vapor.

Figure 2:
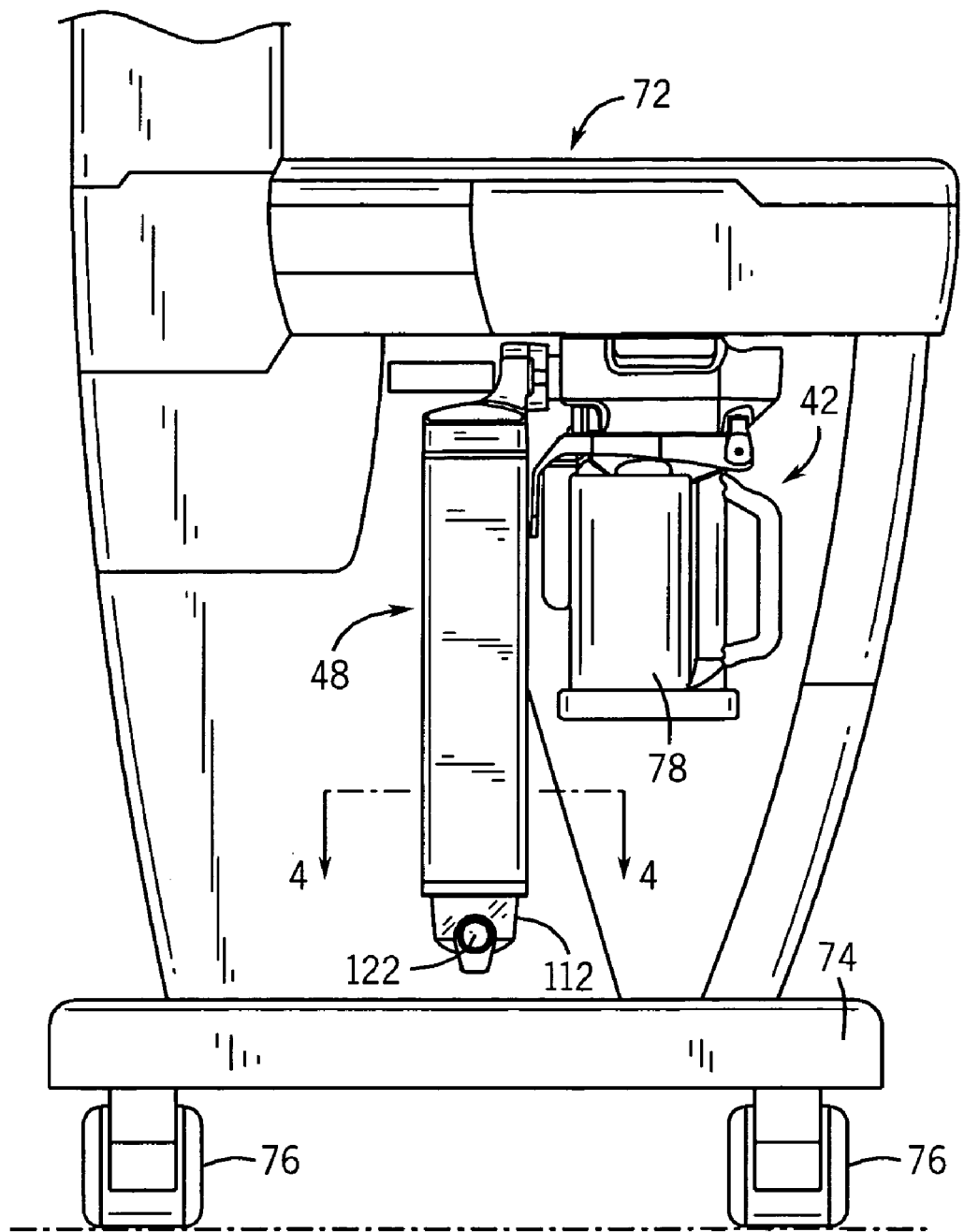
FIG. 2 is a partial side view of a ventilator including the heat exchanger.

FIG. 2 illustrates a conventional integrated ventilator and anesthesia machine 72. The anesthesia machine 72 includes a base 74 having a plurality of wheels 76 that allow the machine 72 to be easily transported. The anesthesia machine 72 includes a $CO_2$ canister 78 that removes $CO_2$ from the breathing gases as previously described. As illustrated, the anesthesia machine includes the heat exchanger 48 positioned downstream from the $CO_2$ absorber 42 to remove moisture from the breathing gases and reduce the temperature of the breathing gases prior to delivery of the breathing gases to the inspiration limb.

Figure 3:
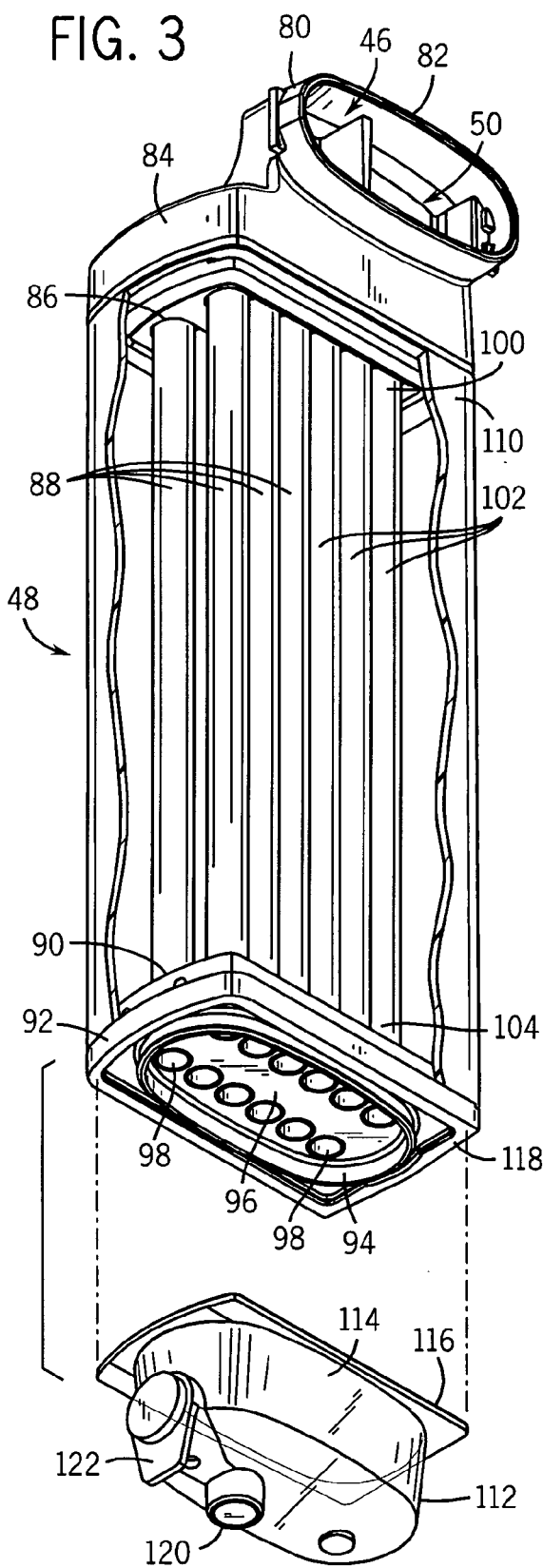
FIG. 3 is an exploded, partial section view of the heat exchanger depicted in FIG. 2.

Referring now to FIG. 3, thereshown are the details of the heat exchanger 48. The heat exchanger 48 includes an interface flange 80 having a flexible seal to form an airtight seal with both the outlet of the $CO_2$ absorber and the inspiration limb of the breathing circuit. The interface flange 80 is formed as part of a top cap 84 that includes an internal passage in fluid communication with the inlet 46 of the heat exchanger. The top cap 84 receives the upper, first end 86 of a plurality of inflow tubes 88. Each of the inflow tubes 88 extends from a first end 86 to a second end 90. In the embodiment of the invention illustrated, the heat exchanger 48 includes six inflow tubes, although various numbers of inflow tubes 88 are contemplated as being within the embodiment of the invention illustrated.

The second end 90 of each inflow tube 88 is received within the lower base 92 of the heat exchanger. The lower base 92 includes a flexible sealing ring 94 surrounding a lower wall 96 having openings 98 sized to correspond to the series of inflow tubes 88.

The top cap 84 of the heat exchanger 48 also includes the heat exchange outlet 50, which is in fluid communication with a second end 100 of each of a plurality of outflow tubes 102. In the embodiment of the invention illustrated in FIG. 3, the heat exchanger 48 includes six outflow tubes 102 positioned immediately adjacent to the six inflow tubes 88. The orientation and number of inflow and outflow tubes 88, 102 could be varied depending upon the specific requirements for the heat exchanger 48.

The first end 104 of each outflow tube 102 is received within the lower base 92 and is aligned with one of the openings 98 included in the lower wall 96. As clearly shown in FIG. 3, the sealing ring 94 completely surrounds each of the openings 98 formed in the lower wall 96.

Figure 4:
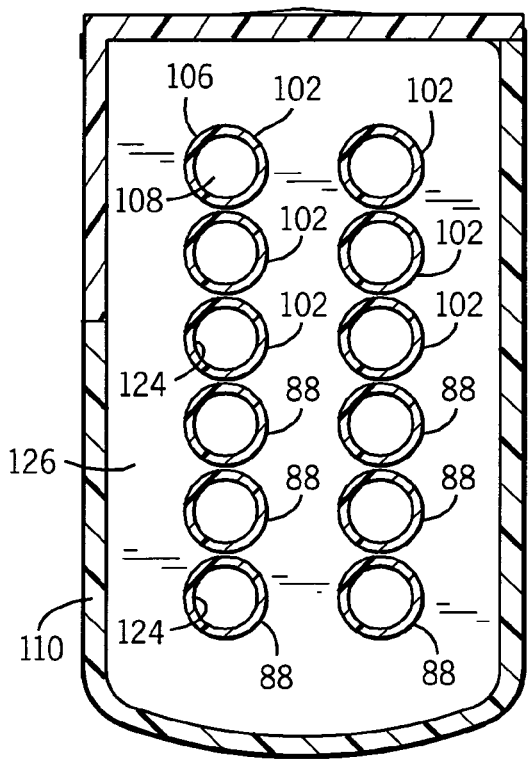
FIG. 4 is a section view taken along line 4-4 of FIG. 2.

In the embodiment of the invention illustrated in FIGS. 3 and 4, each of the inflow tubes 88 and outflow tubes 102 is formed by an outer wall 106 that defines an open interior 108. In the embodiment of the invention illustrated, the cross-sectional flow area of the combination of the six tubes 88, 102 is 471 mm². This cross-sectional area maximizes the surface area and minimizes the flow resistance for the breathing gas passing through each of the tubes 88, 102.

Steady state heat flow is expressed by Fourier's equation:

$$Q = kA \frac{\Delta T}{d}$$

Q=rate of heat flow
k=thermal conductivity
A=contact area
ΔT=temperature difference
d=distance of heat flow As the above equation indicates, the rate of heat flow Q depends upon the contact area A and the distance d of heat flow. Thus, the length, number of tubes and size of each tube affects the rate of heat flow within the heat exchanger 48. In the embodiment of the invention illustrated, each of the tubes 88, 102 has a length of approximately 270 mm and a cross-section area of 78.5 mm².

In the embodiment of the invention illustrated in FIGS. 3 and 4, each of the tubes 88, 102 is formed from a polyester material, such as Hytrel® available from Smooth-Bor. The polyester material used to form each of the heat exchanger tubes 88, 102 provides for efficient heat transfer between the breathing gases contained within the tubes and the ambient air. Although polyester is described as being the preferred embodiment, other materials could be used in accordance with the present invention. In addition, although each of the inflow tubes 88 and outflow tubes 102 are shown as having a smooth outer wall, it is contemplated that each of the tubes could include pleats to enhance the surface area of the tube, thereby increasing the rate of heat flow from the breathing gas to atmosphere.

Referring back to FIG. 3, the heat exchanger 48 includes an outer cover 110 that extends between the top cap 84 and the lower base 92 to provide a visually appealing appearance to the heat exchanger 48.

As illustrated in FIG. 3, the heat exchanger 48 receives a sump 112 that is positioned to collect and retain the moisture condensed out of the breathing gases as the breathing gases flow through the inflow tubes 88 and outflow tubes 102. The sump 112 includes a lower well 114 extending below a top flange 116. The top flange 116 is received within an outer rim 118 formed on the lower base 92. A seal formed as part of the sealing ring 94 engages the opening to the lower well 114 to provide a fluid and gastight seal between the sump 112 and the heat exchanger 48. The sump 112 includes a drain 120 that can be connected to a hose or pan for emptying the well 114. A drain button 122 is included as part of the well 114 and can be depressed to allow water to flow through the drain 120.

Preferably, the outer wall forming the well 114 is formed from a clear, plastic material such that an operator can determine when the well 114 has filled with water.

During operation of the heat exchanger 48, the breathing gases from the $CO_2$ absorber 42 flow into the heat exchanger through the inlet 46. The breathing gases flow through the top cap 84 and into the first end 86 of each of the plurality of inflow tubes 88. As the breathing gases flow downward through the inflow tubes 88, the outer surface of each of the inflow tubes 88 is in contact with ambient, room temperature air. Since the temperature of the breathing gases from the $CO_2$ absorber are in the range of the 36°-38° C. and room temperature is typically 21° C., heat is removed from the flow of breathing gases within the inflow tubes 88. As the temperature of the breathing gases is reduced, water vapor within the breathing gases condenses from the breathing gases and collects along the inner surface 124 of the inflow tubes 88, as shown in FIG. 4.

Since each of the inflow tubes 88 extends in a vertical direction, as shown in FIG. 3, the condensed water contained on the inner surface of each inflow tube 88 flows downward toward the second end 90 and eventually is collected within the well 114 of the sump 112.

After the breathing gases exit the inflow tubes 88, the breathing gases enter into the sump 112 and flow into the first end 104 of each of the plurality of outflow tubes 102. The breathing gases then travel in an upward direction toward the second end 100 of each outflow tube 102. As the breathing gases flow in this upward direction, additional heat is removed from the breathing gases and additional water vapor condenses along the inner surface 124 of each of the outflow tubes 102. Once again, the vertical orientation of the outflow tubes 102 causes the water vapor to flow downward and be collected within the sump 112.

Referring now to FIG. 4, the outer cover 110 defines an open interior 126 that surround each of the inflow tubes 88 and outflow tubes 102. In the embodiment of the invention illustrated, the open interior 126 receives a flow of room temperature ambient air that aids in removing heat from the breathing gases. Alternatively, the open interior 126 could receive a flow of air at a temperature lower than room temperature to aid in removing additional heat, and thus moisture, from the breathing gases.

In addition to reducing the temperature of the breathing gases and removing moisture from the breathing gases, the heat exchanger 48 also acts as a holding area for the fresh gas from the anesthesia machine 52 during the expiration phase of the breathing cycle. Specifically, during the expiration phase, the fresh gas from the anesthesia machine 52, are drawn along the path of least resistance and flow toward the bellows assembly 58. In a closed breathing circuit not including the heat exchanger 48, the fresh gas from the anesthesia machine can flow back into the $CO_2$ absorber 42. Since the output gases from the anesthesia machine 52 are typically very dry and may include an anesthetic agent, the backward flow of these gases into the $CO_2$ absorber 42 can create undesirable problems.

When the heat exchanger 42 is positioned in the closed breathing circuit 14, the output gases from the anesthesia machine 52 are first drawn into the outflow tubes and inflow tubes 88 of the heat exchanger 48 during exhalation of the patient. The combined volume of the inflow and outflow tubes within the heat exchanger 48 is sufficient to receive and hold the volume of gas from the anesthesia machine 52 during the expiration phase of the breathing cycle. The heat exchanger prevents the gases from the anesthesia machine 52 from entering into the $CO_2$ absorber 42. Thus, the heat exchanger 48 serves as a buffer between the anesthesia machine 52 and the CO$_2$ absorber 42 during the expiration phase of the breathing cycle.

As understood in FIG. 3, the sump 112 can be selectively removed from the remaining portions of the heat exchanger 48 for cleaning or other purposes. Additionally, a sump 112 having a larger well 114 could be utilized to collect larger volumes of water from the heat exchanger 48, which would require less frequent drainings of the sump 112.

Various alternatives and embodiments are contemplated as being within the scope of the following claims particularly pointing out and distinctly claiming the subject matter regarded as the invention.

What is claimed is:

1. A breathing circuit for a patient, the breathing circuit comprising:
    an inspiration limb providing breathing gases for supply to the patient;
    an expiration limb receiving breathing gases from the patient;
    means for circulating breathing gases in the breathing circuit to supply breathing gases to the patient and to receive breathing gases expired from the patient;
    a CO$_2$ absorber positioned in the breathing circuit between the expiration limb and the inspiration limb for removing CO$_2$ from the breathing gases expired by the patient;
    a heat exchanger positioned downstream from the CO$_2$ absorber for reducing the temperature of the breathing gases and removing moisture from the breathing gases after the breathing gases exit the CO$_2$ absorber and prior to delivery of the breathing gases to the inspiration limb; and
    a sump separate from the heat exchanger and mounted to the heat exchanger, the sump positioned below the heat exchanger to collect moisture removed from the breathing gases as the breathing gases pass through the heat exchanger, the sump including a drainage valve,
    wherein the heat exchanger comprises:
    a plurality of vertically oriented inflow tubes passing through an open interior of the heat exchanger, each inflow tube having a first end in fluid communication with the CO$_2$ absorber and a second end in fluid communication with the sump;
    a plurality of vertically oriented outflow tubes passing through the open interior of the heat exchanger, each outflow tube having a first end in fluid communication with the sump and a second end in fluid communication with the inspiration limb,
    wherein the temperature within the open interior of the heat exchanger is below the temperature of the breathing gases in both the inflow and outflow tubes to reduce the temperature of the breathing gases as the breathing gases pass through the inflow and outflow tubes.

2. The breathing circuit of claim 1 wherein the breathing gases flow from the second end of the inflow tubes into the sump and from the sump into the first end of the outflow tubes.

3. The breathing circuit of claim 1 wherein the inflow tubes and the outflow tubes are each formed from polyester.

4. The breathing circuit of claim 1 wherein the plurality of inflow tubes and the plurality of outflow tubes each have an outer surface in fluid contact with room temperature air in the open interior of the heat exchanger.

5. The breathing circuit of claim 1 wherein the heat exchanger and sump are removably positioned within the breathing circuit.

6. The breathing circuit of claim 1 wherein the sump is removably attachable to the heat exchanger.

7. The breathing circuit of claim 1 wherein the inflow tubes and the outflow tubes extend in opposite directions.

8. A breathing circuit for a patient, the breathing circuit comprising:
    an inspiration limb providing breathing gases for supply to the patient;
    an expiration limb receiving breathing gases from the patient;
    means for circulating breathing gases in the breathing circuit to supply breathing gases to the patient and to receive breathing gases expired from the patient;
    a CO$_2$ absorber positioned in the breathing circuit between the expiration limb and the inspiration limb for removing CO$_2$ from the breathing gases expired by the patient;
    a heat exchanger positioned downstream from the CO$_2$ absorber for reducing the temperature of the breathing gases and removing moisture from the breathing gases after the breathing gases have passed through the CO$_2$ absorber and prior to delivery of the breathing gases to the inspiration limb,
    wherein the heat exchanger includes a plurality of tubes that receive the breathing gases from the CO$_2$ absorber and direct the breathing gases to the inspiration limb, wherein water vapor entrained within the breathing gases condenses within the plurality of tubes within the heat exchanger; and
    a sump removably attachable to the heat exchanger, the sump positioned below the heat exchanger to collect moisture condensed out of the breathing gases as the breathing gases pass through the heat exchanger, the sump including a drainage valve selectively operable to drain the collected moisture from the sump, wherein the sump is removable and replaceable relative to the heat exchanger.

9. The breathing circuit of claim 8 wherein the plurality of tubes are each formed from polyester.

10. The breathing circuit of claim 8 wherein the plurality of tubes within the heat exchanger comprise:
    a plurality of inflow tubes each having a first end in fluid communication with the CO$_2$ absorber and a second end in fluid communication with the sump; and
    a plurality of outflow tubes each having a first end in fluid communication with the sump and a second end in fluid communication with the inspiration limb.

11. The breathing circuit of claim 10 wherein the breathing gases flow from the second end of the inflow tubes into the sump and from the sump into the first end of the outflow tubes.

12. The breathing circuit of claim 10 wherein the inflow tubes and the outflow tubes extend in opposite directions.

13. The breathing circuit of claim 10 further comprising:
    an anesthesia machine positioned in communication with the inspiration limb of the breathing circuit, wherein the second end of each outflow tube is in fluid communication with the anesthesia machine.

14. The breathing circuit of claim 13 wherein the gases from the anesthesia machine are received within the outflow tubes and the inflow tubes of the heat exchanger during expiration by the patient.

15. A breathing circuit for a patient, the breathing circuit comprising:
    an inspiration limb providing breathing gases for supply to the patient;
    an expiration limb receiving breathing gases from the patient;
    a ventilator for circulating breathing gases in the breathing circuit to supply breathing gases to the patient and to receive breathing gases expired from the patient;

a CO$_2$ absorber positioned in the breathing circuit between the expiration limb and the inspiration limb for removing CO$_2$ gases from the breathing gases expired by the patient;

a heat exchanger positioned downstream from the CO$_2$ absorber for reducing the temperature of the breathing gases and removing moisture from the breathing gases after the breathing gases have passed through the CO$_2$ absorber and prior to delivery of the breathing gases to the inspiration limb, wherein the heat exchanger includes a plurality of inflow tubes that receive the breathing gases from the CO$_2$ absorber and pass through an open interior of the heat exchanger and a plurality of outflow tubes that receive the breathing gases from the inflow tubes and pass through the open interior to direct the breathing gases to the inspiration limb, the plurality of inflow and outflow tubes being vertically oriented within the open interior of the heat exchanger when receiving the breathing gases, wherein the temperature within the open interior of the heat exchanger is above the temperature of the breathing gases such that water vapor entrained within the breathing gases condenses within the plurality of inflow and outflow tubes within the heat exchanger and flows downward along the length of the plurality of inflow and outflow tubes; and a sump operatively positioned below the plurality of tubes to collect moisture condensed out of the breathing gases.

16. The breathing circuit of claim 15 further comprising an anesthesia machine positioned in communication with the inspiration limb of the breathing circuit, wherein the second end of each outflow tube is in fluid communication with the anesthesia machine.

17. The breathing circuit of claim 15 further comprising a drainage valve in the sump, the drainage valve being operable to drain the collected moisture from the sump.

* * * * *

UNITED STATES PATENT AND TRADEMARK OFFICE
CERTIFICATE OF CORRECTION

PATENT NO. : 7,591,267 B2 Page 1 of 1
APPLICATION NO. : 11/220333
DATED : September 22, 2009
INVENTOR(S) : Mashak et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 751 days.

Signed and Sealed this

Twenty-first Day of September, 2010

David J. Kappos
*Director of the United States Patent and Trademark Office*